(12) United States Patent
Peng et al.

(10) Patent No.: US 8,851,069 B2
(45) Date of Patent: Oct. 7, 2014

(54) INHALER

(75) Inventors: Weidong Peng, Bristol (GB);
Christopher Andrew Townsend,
Gloucester (GB)

(73) Assignee: Innovata Biomed Limited, Edinburgh (GB)

( * ) Notice: Subject to any disclaimer, the term of this patent is extended or adjusted under 35 U.S.C. 154(b) by 1874 days.

(21) Appl. No.: 11/578,935

(22) PCT Filed: Apr. 21, 2005

(86) PCT No.: PCT/GB2005/001538
§ 371 (c)(1),
(2), (4) Date: Oct. 19, 2006

(87) PCT Pub. No.: WO2005/102429
PCT Pub. Date: Nov. 3, 2005

(65) Prior Publication Data
US 2007/0246044 A1    Oct. 25, 2007

(30) Foreign Application Priority Data

Apr. 21, 2004  (GB) .................................. 0408817.5
Nov. 4, 2004   (GB) .................................. 0424400.0
Dec. 8, 2004   (GB) .................................. 0426910.6

(51) Int. Cl.
*A61M 16/00*  (2006.01)
*A61M 15/00*  (2006.01)
*B05D 7/14*   (2006.01)
*B65D 83/06*  (2006.01)

(52) U.S. Cl.
CPC ....... *A61M 15/0065* (2013.01); *A61M 2206/14* (2013.01); *A61M 2202/064* (2013.01); *A61M 2206/16* (2013.01); *A61M 15/0003* (2013.01)
USPC ............ 128/203.15; 128/203.12; 128/203.23; 128/203.22

(58) Field of Classification Search
CPC ... A61M 11/001; A61M 11/00; A61M 13/00; A61M 15/00; A61M 15/0003; A61M 15/0006; A61M 15/0086; A61M 15/08
USPC ............ 128/203.12, 203.15, 203.23, 203.21, 128/203.22
See application file for complete search history.

(56) References Cited

U.S. PATENT DOCUMENTS 1,858,735 A   5/1932   Goodsell
2,587,215 A   2/1952   Priestly
(Continued)

FOREIGN PATENT DOCUMENTS

CA   2195065 C   2/2002
CA   2239292 C   9/2003
(Continued)

OTHER PUBLICATIONS

Gerrity, T.R., "Pathophysiological and Disease Constraints on Aerosol Delivery," Chapter 1, Respiratory Drug Delivery I, ed. Byron, P.R., CRC Press, pp. 1-38 (1990).

*Primary Examiner* — Justine Yu
*Assistant Examiner* — Colin W Stuart
(74) *Attorney, Agent, or Firm* — LeClairRyan, a Professional Corporation

(57) ABSTRACT

A dry powder inhaler comprises an airway (1) along which, in use, air is drawn from an upstream, inlet end (2) to a downstream, outlet end (3). The airway (1) includes a medicament presentation region (4) at which, in use, a dose of medicament is presented to the airway (1), a primary air inlet (10), and a barrel (5) extending from the medicament presentation region (4) to the outlet end (3) of the airway (1). The inlet end of the barrel (5) is of reduced internal dimension relative to the medicament presentation region (4) and relative to the outlet end of the barrel (5), such that the inlet end of the barrel (5) constitutes a constriction of the airway (1). At least one secondary air inlet (11) is disposed such that, in use, air enters the airway (1) from the secondary air inlet (11) in a direction that is substantially orthogonal to the direction of flow of air along said barrel (5).

32 Claims, 4 Drawing Sheets

(56) References Cited

U.S. PATENT DOCUMENTS

| | | |
|---|---|---|
| 3,008,609 A | 11/1961 | Sessions |
| 3,439,823 A | 4/1969 | Morane |
| 3,798,054 A | 3/1974 | Kawata et al. |
| 3,854,626 A | 12/1974 | Krechmar |
| 3,874,381 A | 4/1975 | Baum |
| 3,876,269 A | 4/1975 | Fisher et al. |
| 4,047,635 A | 9/1977 | Bennett, Jr. |
| 4,114,615 A | 9/1978 | Wetterlin |
| 4,174,034 A | 11/1979 | Hoo |
| 4,200,099 A | 4/1980 | Guenzel et al. |
| 4,274,403 A | 6/1981 | Struve |
| 4,524,769 A | 6/1985 | Wetterlin |
| 4,534,343 A | 8/1985 | Nowacki et al. |
| 4,570,630 A | 2/1986 | Elliott et al. |
| 4,604,847 A | 8/1986 | Moulding, Jr. et al. |
| 4,624,442 A | 11/1986 | Duffy et al. |
| 4,627,432 A | 12/1986 | Newell et al. |
| 4,635,829 A | 1/1987 | Brittingham, Jr. |
| 4,668,218 A | 5/1987 | Virtanen |
| 4,811,731 A | 3/1989 | Newell et al. |
| 4,860,740 A | 8/1989 | Kirk et al. |
| 4,882,210 A | 11/1989 | Romberg et al. |
| 4,895,719 A | 1/1990 | Radhakrishnan et al. |
| 4,907,583 A | 3/1990 | Wetterlin et al. |
| 4,934,358 A | 6/1990 | Nilsson et al. |
| 4,950,365 A | 8/1990 | Evans |
| 5,002,048 A | 3/1991 | Makiej, Jr. |
| 5,007,419 A | 4/1991 | Weinstein et al. |
| 5,042,472 A | 8/1991 | Bunin |
| 5,053,237 A | 10/1991 | Hendricks et al. |
| 5,064,083 A | 11/1991 | Alexander et al. |
| 5,067,491 A | 11/1991 | Taylor, II et al. |
| 5,113,855 A | 5/1992 | Newhouse |
| 5,152,422 A | 10/1992 | Springer |
| 5,154,326 A | 10/1992 | Chang et al. |
| 5,161,524 A | 11/1992 | Evans |
| 5,169,029 A | 12/1992 | Behar et al. |
| 5,192,528 A | 3/1993 | Radhakrishnan et al. |
| 5,207,217 A | 5/1993 | Cocozza et al. |
| 5,208,226 A | 5/1993 | Palmer |
| 5,253,782 A | 10/1993 | Gates et al. |
| 5,263,475 A | 11/1993 | Altermatt et al. |
| 5,295,479 A | 3/1994 | Lankinen |
| 5,301,666 A | 4/1994 | Lerk et al. |
| 5,347,999 A | 9/1994 | Poss et al. |
| 5,351,683 A | 10/1994 | Chiesi et al. |
| 5,394,868 A | 3/1995 | Ambrosio et al. |
| 5,409,132 A | 4/1995 | Kooijmans et al. |
| 5,411,175 A | 5/1995 | Armstrong et al. |
| 5,415,162 A | 5/1995 | Casper et al. |
| 5,435,301 A | 7/1995 | Herold et al. |
| 5,437,267 A | 8/1995 | Weinstein et al. |
| 5,437,270 A | 8/1995 | Braithwaite |
| 5,447,151 A | 9/1995 | Bruna et al. |
| 5,450,160 A | 9/1995 | Tianello et al. |
| 5,458,135 A | 10/1995 | Patton et al. |
| 5,485,939 A | 1/1996 | Tucker |
| 5,503,144 A | 4/1996 | Bacon |
| 5,520,166 A | 5/1996 | Ritson et al. |
| 5,524,613 A | 6/1996 | Haber et al. |
| 5,551,597 A | 9/1996 | Lambelet, Jr. et al. |
| 5,562,231 A | 10/1996 | Lambelet, Jr. et al. |
| 5,562,918 A | 10/1996 | Stimpson |
| 5,575,280 A | 11/1996 | Gupte et al. |
| 5,617,845 A | 4/1997 | Poss et al. |
| 5,622,166 A | 4/1997 | Eisele et al. |
| 5,653,227 A | 8/1997 | Barnes et al. |
| 5,657,748 A | 8/1997 | Braithwaite |
| 5,657,794 A | 8/1997 | Briner et al. |
| 5,664,557 A | 9/1997 | Makiej, Jr. |
| 5,664,697 A | 9/1997 | Lambelet, Jr. et al. |
| 5,676,130 A | 10/1997 | Gupte et al. |
| 5,678,538 A | 10/1997 | Drought |
| D389,570 S | 1/1998 | Savolainen |
| 5,740,792 A | 4/1998 | Ashley et al. |
| 5,740,794 A | 4/1998 | Smith et al. |
| 5,775,536 A | 7/1998 | Lambelet, Jr. et al. |
| 5,778,873 A | 7/1998 | Braithwaite |
| 5,785,049 A | 7/1998 | Smith et al. |
| 5,799,821 A | 9/1998 | Lambelet, Jr. et al. |
| 5,857,457 A | 1/1999 | Hyppölä |
| 5,875,776 A | 3/1999 | Vaghefi |
| 5,881,719 A | 3/1999 | Gottenauer et al. |
| 5,896,855 A | 4/1999 | Hobbs et al. |
| 5,904,139 A | 5/1999 | Hauser |
| 5,906,198 A * | 5/1999 | Flickinger .............. 128/200.21 |
| 5,921,237 A | 7/1999 | Eisele et al. |
| 5,924,417 A | 7/1999 | Braithwaite |
| 5,941,241 A | 8/1999 | Weinstein et al. |
| 5,944,660 A | 8/1999 | Kimball et al. |
| 5,955,439 A | 9/1999 | Green |
| 5,981,549 A | 11/1999 | Viner |
| 5,996,577 A | 12/1999 | Ohki et al. |
| 6,006,747 A | 12/1999 | Eisele et al. |
| 6,035,463 A | 3/2000 | Pawelzik et al. |
| 6,065,471 A | 5/2000 | Schaeffer et al. |
| 6,065,472 A | 5/2000 | Anderson et al. |
| 6,076,521 A | 6/2000 | Lindahl et al. |
| 6,089,227 A | 7/2000 | Nilsson |
| 6,116,238 A | 9/2000 | Jackson et al. |
| 6,116,239 A | 9/2000 | Volgyesi |
| 6,119,688 A | 9/2000 | Whaley et al. |
| 6,125,844 A | 10/2000 | Samiotes |
| 6,138,668 A | 10/2000 | Patton et al. |
| 6,158,675 A | 12/2000 | Ogi |
| 6,196,218 B1 | 3/2001 | Voges |
| 6,220,243 B1 | 4/2001 | Schaeffer et al. |
| 6,230,707 B1 * | 5/2001 | Horlin ...................... 128/203.15 |
| 6,234,167 B1 | 5/2001 | Cox et al. |
| 6,240,918 B1 | 6/2001 | Ambrosio et al. |
| 6,254,854 B1 | 7/2001 | Edwards et al. |
| 6,273,085 B1 | 8/2001 | Eisele et al. |
| 6,321,747 B1 | 11/2001 | Dmitrovic et al. |
| 6,324,428 B1 | 11/2001 | Weinberg et al. |
| 6,325,241 B1 | 12/2001 | Garde et al. |
| 6,328,034 B1 | 12/2001 | Eisele et al. |
| 6,347,629 B1 | 2/2002 | Braithwaite |
| 6,418,926 B1 | 7/2002 | Chawla |
| 6,443,146 B1 | 9/2002 | Voges |
| 6,484,718 B1 | 11/2002 | Schaeffer et al. |
| 6,523,536 B2 | 2/2003 | Fugelsang et al. |
| 6,543,443 B1 | 4/2003 | Klimowicz et al. |
| 6,553,987 B1 | 4/2003 | Davies |
| 6,557,550 B1 | 5/2003 | Clarke |
| 6,557,552 B1 | 5/2003 | Cox et al. |
| 6,601,729 B1 | 8/2003 | Papp |
| 6,616,914 B2 | 9/2003 | Ward et al. |
| 6,675,839 B1 | 1/2004 | Braithwaite |
| 6,698,425 B1 | 3/2004 | Widerström |
| 6,810,873 B1 | 11/2004 | Haikarainen et al. |
| 6,810,874 B1 | 11/2004 | Koskela et al. |
| 6,845,772 B2 | 1/2005 | Braithwaite et al. |
| 6,926,003 B2 | 8/2005 | Seppälä |
| 7,143,765 B2 * | 12/2006 | Asking et al. ............ 128/203.15 |
| 7,278,982 B2 * | 10/2007 | Tsutsui ........................ 604/58 |
| 2002/0092523 A1 * | 7/2002 | Connelly et al. ......... 128/203.15 |
| 2003/0075172 A1 | 4/2003 | Johnson et al. |
| 2003/0116157 A1 | 6/2003 | Braithwaite et al. |
| 2003/0136406 A1 | 7/2003 | Seppala |
| 2004/0011357 A1 | 1/2004 | Braithwaite |
| 2004/0035412 A1 | 2/2004 | Staniforth et al. |
| 2004/0101482 A1 | 5/2004 | Sanders |
| 2004/0236282 A1 | 11/2004 | Braithwaite |
| 2004/0251318 A1 | 12/2004 | Braithwaite |
| 2005/0121023 A1 | 6/2005 | Braithwaite |

FOREIGN PATENT DOCUMENTS

| | | |
|---|---|---|
| DE | 14 98 398 | 1/1969 |
| DE | 23 46 730 A | 4/1975 |
| DE | 32 43 731 A | 5/1984 |
| DE | 195 30 240 | 2/1997 |
| DE | 197 57 207 A1 | 6/1999 |
| EP | 0 045 522 A2 | 2/1982 |

(56) References Cited

FOREIGN PATENT DOCUMENTS

| | | |
|---|---|---|
| EP | 0 079 478 A1 | 5/1983 |
| EP | 0 166 294 B1 | 10/1989 |
| EP | 0 372 777 B1 | 6/1990 |
| EP | 0 424 790 B1 | 5/1991 |
| EP | 0 448 204 B1 | 9/1991 |
| EP | 0 469 814 A1 | 2/1992 |
| EP | 0 514 085 B1 | 11/1992 |
| EP | 0 520 440 A1 | 12/1992 |
| EP | 0 539 469 B1 | 5/1993 |
| EP | 0 548 605 B1 | 6/1993 |
| EP | 0 573 128 A2 | 12/1993 |
| EP | 0 626 689 BI | 11/1994 |
| EP | 0 659 432 A1 | 6/1995 |
| EP | 0 663 815 B1 | 7/1995 |
| EP | 1 062 962 A | 12/2000 |
| EP | 1 106 196 A | 6/2001 |
| EP | 1 208 863 A | 5/2002 |
| EP | 1291032 A2 | 12/2003 |
| EP | 1452198 A1 | 1/2004 |
| FR | 2 516 387 A | 5/1983 |
| FR | 2 584 604 A | 1/1987 |
| FR | 2 662 936 A | 12/1991 |
| FR | 2 753 791 A1 | 3/1998 |
| GB | 3908 | 0/1911 |
| GB | 1 242 211 | 8/1971 |
| GB | 1 573 551 | 8/1980 |
| GB | 2 041 763 A | 9/1980 |
| GB | 2 165 159 A | 4/1986 |
| GB | 2 178 965 A | 2/1987 |
| GB | 2 235 753 A | 3/1991 |
| GB | 2 248 400 A | 4/1992 |
| GB | 2 366 208 A | 3/2002 |
| JP | 2002/165884 | 6/2002 |
| WO | WO 90/07351 | 7/1990 |
| WO | WO 91/04011 | 4/1991 |
| WO | WO 91/11173 | 8/1991 |
| WO | WO 91/11495 | 8/1991 |
| WO | WO 91/14422 | 10/1991 |
| WO | WO 92/00771 A | 1/1992 |
| WO | WO 92/03175 | 3/1992 |
| WO | WO 92/04928 | 4/1992 |
| WO | WO 92/09322 | 6/1992 |
| WO | WO 92/18188 | 10/1992 |
| WO | WO 93/00951 | 1/1993 |
| WO | WO 93/11746 | 6/1993 |
| WO | WO 93/16748 | 9/1993 |
| WO | WO 95/00128 | 1/1995 |
| WO | WO 95/15777 | 6/1995 |
| WO | 95/17917 A1 | 7/1995 |
| WO | 96/02231 A1 | 2/1996 |
| WO | 96/08284 A2 | 3/1996 |
| WO | WO 97/00399 | 1/1997 |
| WO | 97/20589 A1 | 6/1997 |
| WO | 97/40819 A1 | 11/1997 |
| WO | WO 98/26828 | 6/1998 |
| WO | 98/28033 A2 | 7/1998 |
| WO | WO 98/30262 | 7/1998 |
| WO | WO 98/31352 | 7/1998 |
| WO | WO 99/12597 | 3/1999 |
| WO | WO 99/13930 | 3/1999 |
| WO | WO 99/26676 | 6/1999 |
| WO | WO 00/12163 | 3/2000 |
| WO | WO 00/45878 | 8/2000 |
| WO | WO 00/64519 | 11/2000 |
| WO | WO 01/17595 A1 | 3/2001 |
| WO | 01/28887 A1 | 4/2001 |
| WO | WO 01/39823 A | 6/2001 |
| WO | WO 01/51030 A1 | 7/2001 |
| WO | WO 01/60341 A1 | 8/2001 |
| WO | 01/87391 A2 | 11/2001 |
| WO | WO 01/87378 A2 | 11/2001 |
| WO | 01/97889 A2 | 12/2001 |
| WO | 02/00280 A2 | 1/2002 |
| WO | 02/00281 A2 | 1/2002 |
| WO | WO 02/056948 A | 7/2002 |
| WO | 2004/017914 A2 | 3/2004 |
| WO | 2004/017918 A2 | 3/2004 |
| WO | 2004/017942 A1 | 3/2004 |
| WO | 2004/026380 A2 | 4/2004 |
| WO | 2004/091705 A1 | 10/2004 |
| WO | WO 2004/091705 A | 10/2004 |

\* cited by examiner

# INHALER

This application is a national stage application under 35 U.S.C. §371 from PCT Application No. PCT/GB2005/001538, filed Apr. 21, 2005, which claims the priority benefit of Great Britain Application No. 0408817.5, filed Apr. 21, 2004, Great Britain Application No. 0424400.0, filed Nov. 4, 2004, and Great Britain Application No. 0426910.6, filed Dec. 8, 2004.

This invention relates to a dry powder inhaler, that is to say a device for the administration of powdered medicament by inhalation, and in particular to such an inhaler having a certain form of airway that functions as an aerosolisation device, as well as to methods of treatment related thereto.

The administration of medicaments by inhalation is well-known. A wide variety of medicaments are now administered by that route, for the treatment of a wide variety of respiratory disorders.

Examples of medicaments used for the treatment of respiratory disorders include, among others, anti-allergic agents, eg cromoglycate, ketotifen and nedocromil; anti-inflammatory steroids, eg beclomethasone dipropionate, fluticasone, budesonide, flunisolide, ciclesonide, triamcinolone acetonide and mometasone furoate; bronchodilators such as $\beta_2$-agonists, eg fenoterol, formoterol, pirbuterol, reproterol, salbutamol, salmeterol and terbutaline, non-selective $\beta$-stimulants, eg isoprenaline, and xanthine bronchodilators, eg theophylline, aminophylline and choline theophyllinate; and anticholinergic agents, eg ipratropium bromide, oxitropium bromide and tiotropium.

The most common form in which such medicaments are formulated for administration by inhalation is as a powder. In the past, many such compositions were formulated as pressurised aerosols, in which the powder medicament was suspended in a liquefied propellant. Due to the adverse environmental effects of the propellants conventionally used, however, there is now increased interest in the use of so-called dry powder inhalers (DPIs). In a DPI, a unit dose of medicament powder, either packaged as such or metered from a bulk reservoir of medicament, is presented to an airway and is then entrained in an airflow passing through the airway. The airflow is most commonly generated by the patient's act of inhalation.

For the effective treatment of conditions of the respiratory tract it is generally desirable that as high a proportion of the powder as possible should be in the form of particles that are sufficiently fine that they are able to penetrate deep into the airways, and in particular that they should be transported deep into the lung. An important parameter in assessing the effectiveness of powdered medicament intended for inhalation is therefore the fine particle fraction (FPF), which defines the fraction of the emitted dose from an inhaler that has the potential to be deposited in the lung. This fraction is often defined as the proportion of the medicament that is in the form of particles with a diameter of less than 5 μm.

The FPF will depend to some extent on the manner in which the medicament is formulated, but also is strongly dependent on the performance of the device (inhaler) from which the formulation is delivered.

In optimising the performance of a DPI, a number of conflicting considerations must be addressed. It is generally desirable to create a turbulent airflow, in order to deagglomerate medicament particles that would otherwise adhere to each other in aggregates that are too large to penetrate deep into the lung. In order to achieve this, relatively high flow rates are required. However, the rate of flow of the air and entrained medicament that enters the patient's buccal cavity should not be excessively high, as that can cause the medicament particles simply to be deposited on the surfaces of the oropharynx and hence not to reach the intended site of action.

Numerous attempts have been made to improve the FPF of inhalers, especially DPIs.

For instance, it is well known that agglomeration of medicament particles can cause the FPF to decrease. Therefore, there is a clear incentive to reduce agglomerations. US-A-2004/0035412 describes a mouthpiece for use in an inhaler, the mouthpiece being provided with a number of abutments which extend across the mouthpiece.

The abutments are arranged in a staggered configuration and are intended to cause medicament agglomerations to break up.

Similarly, U.S. Pat. No. 6,681,768 describes a deagglomeration system for an inhaler, which comprises a mouthpiece provided with a plurality of circumferential fins that act as deagglomeration means.

Combination therapy using two different medicaments has in recent years become an increasingly widely accepted method for the treatment of asthma. A number of combination products are now marketed, typically incorporating a long-acting $\beta_2$-agonist and a corticosteroid drug in the same inhaler. DPI products of this type have focussed on combined drug formulations, ie single formulations containing both active ingredients. An alternative approach is to use a device such as that disclosed in WO-A-01/39823. In such a device, separate reservoirs are provided for the two active ingredients and these are delivered via separate airways. This approach offers certain advantages, but presents particular challenges in terms of airway performance. The main reason for this is that only one-half of the overall airflow is available for aerosolisation of each of the two medicaments, and the kinetic energy of the air stream will also be significantly reduced compared to a single airway of similar geometry. Optimisation of airway design is therefore particularly important for such a device.

There has now been devised an improved form of dry powder inhaler that offers improved performance relative to the prior art, and which is particularly useful for the delivery of combinations of different medicaments.

Thus, according to the invention there is provided a dry powder inhaler comprising an airway along which, in use, air is drawn from an upstream, inlet end to a downstream, outlet end, the airway including a medicament presentation region at which, in use, a dose of medicament is presented to the airway, a primary air inlet, and a barrel extending from the medicament presentation region to the outlet end of the airway, wherein (i) the inlet end of the barrel is of reduced internal dimension relative to the medicament presentation region and relative to the outlet end of the barrel, such that the inlet end of the barrel constitutes a constriction of the airway; and (ii) at least one secondary air inlet is provided, said secondary air inlet being disposed such that, in use, air enters the airway from said secondary air inlet in a direction that is substantially orthogonal to the direction of flow of air along said barrel.

The dry powder inhaler according to the invention is advantageous primarily in that medicament entrained at the medicament presentation region is delivered to the user of the inhaler with a high fine particle fraction. This is believed to be due to the generation of a turbulent airflow at the medicament presentation region and a relatively high airflow in that region. The form of the barrel nonetheless leads to a deceleration of the airflow downstream of the medicament presentation region, which reduces deposition of the entrained medicament in the oropharynx. In particular, the reduced dimension of the inlet end of the barrel, constituting a constriction in the airway adjacent to the medicament presentation region, means that the powder flow may be subject to increased initial acceleration whilst maximising dispersion of the medicament, yet allowing deceleration of unagglomerated particles. These benefits are particularly advantageous in DPI devices for the administration of two different medicaments dispensed via separate airways.

Preferably, the medicament presentation region of the airway comprises a substantially enclosed chamber, the walls of which carry the primary and secondary air inlets.

Medicament is preferably presented to the airway by virtue of being delivered to a recess or opening in a wall of the chamber. The nature of the mechanism by which a dose of medicament is delivered to the chamber is not critical to the present invention. Examples of such mechanisms are those disclosed in WO-A-92/00771, WO-A-93/16748 and WO-A-01/39823.

The primary air inlet most preferably has the form of a slot in a wall of the chamber. The slot is preferably disposed transverse to the longitudinal axis of the barrel, and is preferably formed in the wall of the chamber that is opposite to that to which the dose of medicament is presented, such that air is drawn into the chamber with a component of its motion that is directed towards the wall of the chamber at which the medicament is presented. This may assist in the pick-up and entrainment of the medicament.

The secondary air inlet also most preferably has the form of a slot. The secondary air inlet is preferably provided in a wall of the chamber that is orthogonal to the wall at which the medicament is presented.

The flows of air into the chamber from the primary and secondary air inlets are thus preferably orthogonal to each other.

Preferably, the diameter of the barrel increases gradually from the inlet end to the outlet end of the barrel. Thus, the barrel will have a generally frustoconical internal bore.

The internal diameter of the barrel may vary. We have particularly found it to be advantageous that the outlet end should have an internal diameter of 8 mm or less. However, if the air inlet end of the barrel has an internal diameter of from 2 mm to 4 mm, then the outlet end of the barrel will have an internal diameter of from 4 mm to 8 mm.

Deagglomeration of entrained medicament may be further facilitated by the provision on the internal walls of the barrel of grooves or fins. In one such embodiment of the invention, one or more fins protrude from the inner walls of the barrel. Preferably, the barrel is provided with a plurality of fins. The fins may be of substantially the same depth along the whole of their length. However, more preferably, the fins reduce in depth from the inlet end of the barrel to the outlet end.

Optionally, the fins may extend along the full length of the barrel. Alternatively, and preferably, the fins extend along only part of the length of the barrel and terminate before the outlet end of the barrel.

The fins may be substantially linear and may extend substantially parallel to the longitudinal axis of the barrel. Alternatively, the fins may be adapted to impart some degree of rotary motion to the airflow passing along the barrel. Thus, the fins may be wholly or partly helical in form. The barrel may be provided with a combination of axial and helical fins.

The fins may be substantially continuous or may be interrupted. A combination of continuous and/or interrupted fins may be provided.

When the fins are helical, the angle subtended by the helix within the barrel may vary. Preferably, the fins subtend an angle of from 90° to 270°, preferably from 135° to 225° and most preferably about 180°.

The number of fins may also vary. Thus, there may be from 1 to 5 fins, preferably from 2 to 4 and especially 2 or 3 fins.

When a plurality of fins are provided they may or may not be spaced equiangularly apart. However, it is preferred that the fins are equiangularly spaced.

Optimisation of performance may be achieved by appropriate control of the proportions of the overall airflow that enter the medicament presentation region via the primary and secondary air inlets. These proportions may be controlled most easily by appropriate selection of the cross-sectional areas of the various inlets. The ratio of the areas of the primary and secondary air inlets may be important for, inter alia, optimising pickup and entrainment of medicament from the medicament presentation region, the generation of turbulence and/or improving deagglomeration of medicament particles.

Preferably, the ratio of the cross-sectional areas of the primary and secondary air inlets is between 10:1 and 1:1, more preferably between 5:1 and 2:1, eg about 3:1.

The cross-sectional area of the primary air inlet is preferably greater than 2 $mm^2$, more preferably greater than 4 $mm^2$, and is preferably less than 10 $mm^2$, and more preferably less than 8 $mm^2$.

The cross-sectional area of the secondary air inlet is preferably greater than 0.5 $mm^2$, more preferably greater than 1 $mm^2$, and is preferably less than 5 $mm^2$, and more preferably less than 3 $mm^2$.

Generally, the outlet end of the airway will form part of, or will be enclosed within, a mouthpiece that, in use, is placed between the user's lips and via which the medicament is inhaled.

In some prior art devices, such as those sold under the trade marks Diskhaler®, Diskus® and Accuhaler® (available from GlaxoSmithKline), two symmetrical air bleeds are provided in the outlet section of the airway. However, in, for example, the Diskhaler® the positions of those air bleeds are so close to the airway outlet that they may potentially be covered by the patient's mouth when in use. Thus, in the present invention it is preferred that the air inlets are positioned such that, in normal use, they cannot be occluded by the user's lips, or indeed by any other part of the user's anatomy, eg the fingers of the hand in which the device is held by the user.

The inhaler of the invention may comprise any conventionally known dosage units, eg single dosage units or, preferably, a bulk reservoir.

A variety of medicaments may be administered by using the inhaler of the invention. Such medicaments are generally suitable for the treatment of asthma, COPD and respiratory infections. Such medicaments include, but are not limited to $\beta_2$-agonists, eg fenoterol, formoterol, pirbuterol, reproterol, rimiterol, salbutamol, salmeterol and terbutaline; non-selective beta-stimulants such as isoprenaline; xanthine bronchodilators, eg theophylline, aminophylline and choline theophyllinate; anticholinergics, eg ipratropium bromide, oxitropium and tiotropium; mast cell stabilisers, eg sodium cromoglycate and ketotifen; bronchial anti-inflammatory agents, eg nedocromil sodium; and steroids, eg beclomethasone dipropionate, fluticasone, budesonide, flunisolide, triamcinolone, mometasone and ciclesonide, and salts or derivatives thereof.

As mentioned above, the inhaler of the present invention is particularly well suited to the delivery of combinations of separately formulated medicaments. It is particularly preferred that such medicaments be delivered via separate airways. Thus, in a specific aspect of the invention, there is provided a dry powder inhaler comprising a plurality of separate airways along which, in use, air is drawn from an upstream, inlet end to a downstream, outlet end, each airway including a medicament presentation region at which, in use, a dose of medicament is presented to the airway, a primary air inlet, and a barrel extending from the medicament presentation region to the outlet end of the airway, wherein (i) the inlet end of the barrel is of reduced internal dimension relative to the medicament presentation region and relative to the outlet end of the barrel, such that the inlet end of the barrel constitutes a constriction of the airway; and (ii) at least one secondary air inlet is provided, said secondary air inlet being disposed such that, in use, air enters the airway from said secondary air inlet in a direction that is substantially orthogonal to the direction of flow of air along said barrel.

Specific combinations of medicaments which may be mentioned include combinations of steroids and $\beta_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol.

Further medicaments which may be mentioned include systemically active materials, such as, proteinaceous compounds and/or macromolecules, for example, hormones and mediators, such as insulin, human growth hormone, leuprolide and alpha-interferon; growth factors, anticoagulants, immunomodulators, cytokines and nucleic acids.

According to a further aspect of the invention we provide a method of delivering a powder which comprises the use of a dry powder inhaler as hereinbefore described.

We further provide a method of treatment of a patient with a respiratory disorder which comprises the administration of at least one medicament using a dry powder inhaler as hereinbefore described.

We also provide a method of treatment of a patient with a systemic disorder which comprises the administration of a medicament using a dry powder inhaler of the invention.

The invention will now be described in greater detail, by way of illustration only, with reference to the accompanying drawings, in which FIG. 1 is a perspective view of a first embodiment of an airway forming part of a dry powder inhaler according to the invention;

Figure 1:
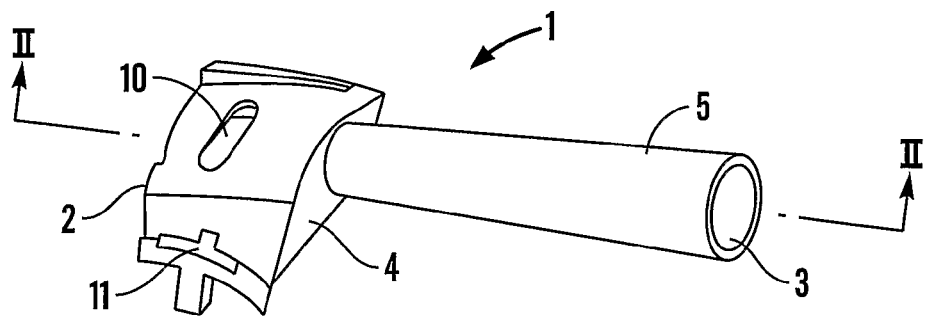

Referring first to FIG. 1, an airway (generally designated 1) for use in a dry powder inhaler has an inlet end 2 and an outlet end 3. The airway 1 acts as an aerosolisation device, air being drawn, in use, by the user of the inhaler into the inlet end 2 of the airway and out of the outlet end 3.

The inlet end 2 of the airway 1 is formed such that when it is brought into conjunction with other components of the inhaler, specifically with a metering device of the inhaler, as described more fully below, a substantially enclosed chamber is formed within which a unit dose of medicament is presented for inhalation. Thus, the inlet end 2 of the airway 1, which is of enlarged dimensions relative to the remainder of the airway 1, constitutes a medicament presentation region 4 of the airway.

A barrel 5 extends from the medicament presentation region 4 to the outlet end 3 of the airway 1. The barrel 5 increases gradually in diameter, the internal diameter of the barrel 5 at the outlet end 3 being approximately 50% greater than that at the inlet end of the barrel 5.

The medicament presentation region 4 is provided with a primary air inlet 10 and a secondary air inlet 11.

Figure 3:
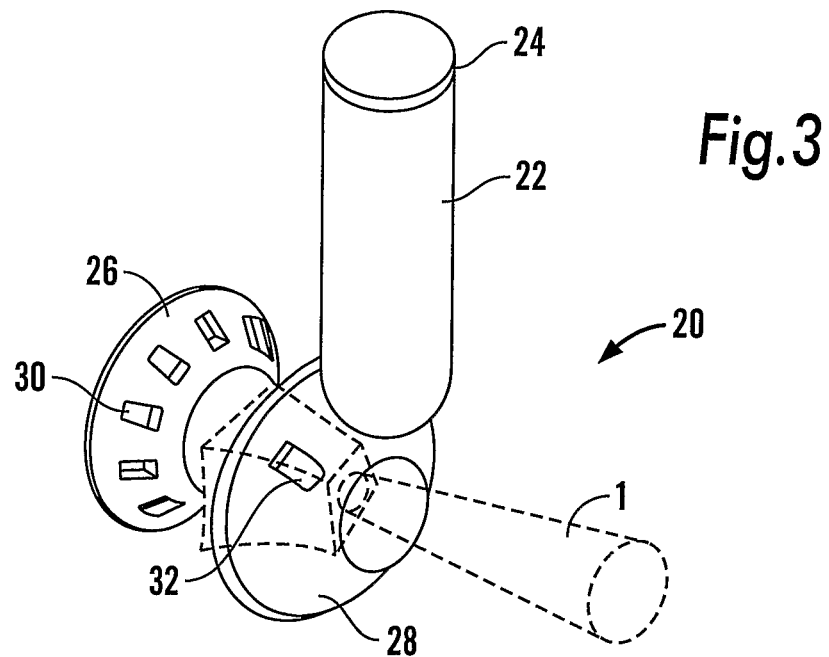
FIG. 3 is a schematic exploded view of components of a dry powder inhaler device, with the location of the airway of FIG. 1 shown in broken lines.
Figure 4:
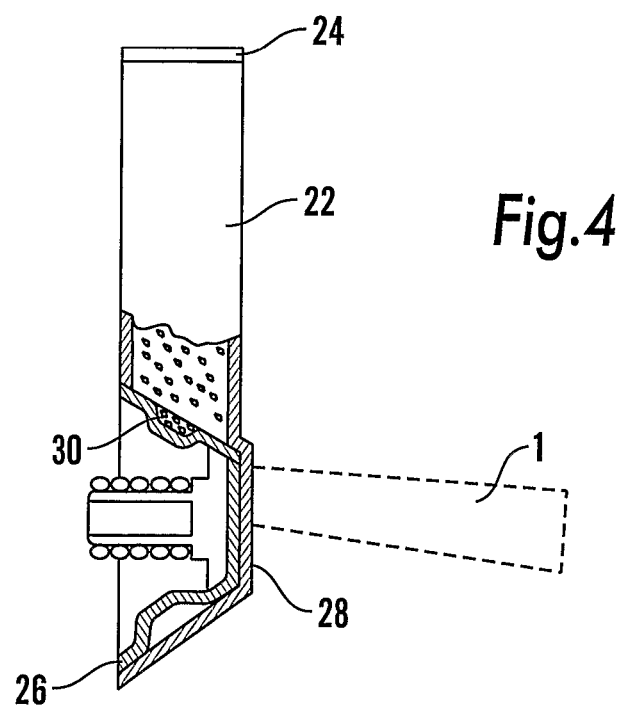
FIG. 4 is a side view, partly in section and partly cut away, corresponding to FIG. 3, again with the location of the airway indicated in broken lines.

FIGS. 3 and 4 illustrate schematically the manner in which the airway 1 is coupled to other components of a dry powder inhaler. It will be appreciated by those skilled in the art that FIGS. 3 and 4 illustrate only schematically the metering mechanism of the inhaler and the manner in which that mechanism is coupled to the airway. Numerous other components would necessarily be present in a complete inhaler, and the nature of form of suitable such components will be readily apparent to those skilled in the art. In general, those other components are not pertinent to the present invention.

Referring to FIG. 3, a dry powder inhaler for the delivery of metered doses of a single medicament formulation is generally designated 20. The inhaler 20 comprises a medicament reservoir 22 in the form of an upright (as viewed in FIG. 3) hollow cylinder that is charged with a bulk quantity of a powdered medicament. The reservoir 22 is closed at the top by a plug 24 and is open at its lower end. A frustoconical metering wheel 26 fits closely within a wheel shroud 28 that is formed integrally with the reservoir 22. The wheel 26 serves to close the open lower end of the reservoir 22.

The frustoconical surface of the wheel 26 is formed with a series of measuring cups 30, and the wheel shroud 28 is formed with an opening 32 of slightly greater dimensions than the measuring cups 30.

The arrangement is such that the wheel 26 is capable of indexed rotation in one direction only within the wheel shroud 28. Twelve measuring cups 30 are formed in the wheel 30, and those cups 30 are equiangularly spaced. The angular separation of the cups 30 is thus 30°, and each indexed rotation of the wheel 30 rotates the wheel by 30°, thus bringing each measuring cup 30 into the position previously (ie before the indexed rotation) occupied by an adjacent cup 30.

At any given time, one of the measuring cups 30 is located beneath the open lower end of the reservoir 22. That cup 30 therefore fills with powdered medicament under the influence of gravity (see FIG. 4). The dimensions of the measuring cup 30 and the formulation of the powdered medicament are selected such that the contents of one such cup 30 constitute the intended unit dose of the medicament.

The opening 32 in the wheel shroud 28 is positioned with an angular separation from the central axis of the reservoir 22 of 60°. Thus, two indexed rotations of the wheel 26 brings a measuring cup 30, filled with a unit dose of the medicament, into registration with the opening 32. The dose of medicament may be flushed out of the measuring cup 30 by an airflow passing across the opening 32. To achieve this, the airway 1 is fitted to the wheel shroud 28, as indicated by the broken lines in FIG. 3.

The medicament presentation region 4 and the external surface of the wheel shroud 28 over which it is fitted thus form a substantially enclosed chamber.

The outlet end of the barrel 5 of the airway 1 constitutes, or is positioned within, a mouthpiece that, in use, is placed between the user's lips. Inhalation by the user causes air to be drawn into the airway through the primary air inlet 10 and secondary air inlet 11. That flow of air causes the dose of medicament to be flushed from the measuring cup 30 located at the opening 32 and to be entrained in the airflow. The flow of air into the medicament presentation region from two different air inlets, viz the primary air inlet 10 and the secondary air inlet 11, that are disposed substantially orthogonally to each other, increases the degree of turbulence in the airflow, improving deagglomeration, entrainment and aerosolisation of the powdered medicament.

The inlet end of the barrel 5, being of reduced dimension relative to the internal dimensions of the medicament presentation region 4 constitutes a restriction in the airway. The effect of this constriction is to cause air passing through the constriction to accelerate, thereby further enhancing deagglomeration of the entrained medicament. However, the widening of the barrel 5 downstream of the constriction causes the airflow to slow down. The airflow therefore exits the barrel 5 at reduced velocity, thereby reducing the tendency for the medicament to deposit in the user's throat and upper airway, and increasing the proportion of the medicament that penetrates deep into the lower airway.

Figure 2:
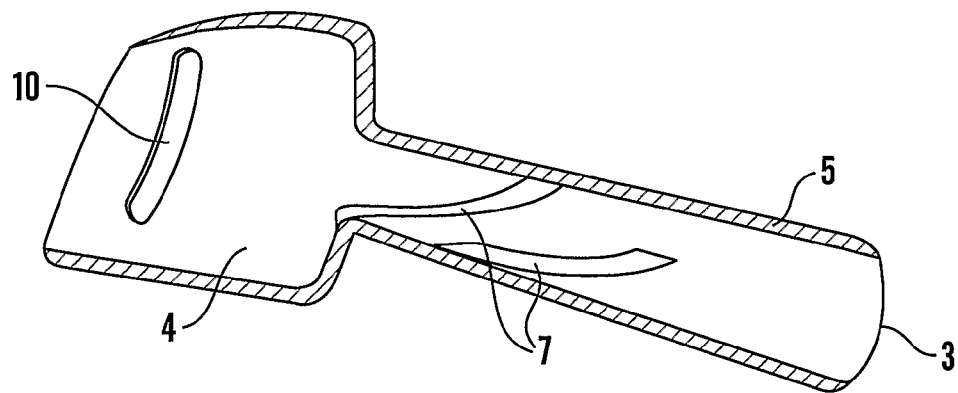
FIG. 2 is a cross-sectional view on the line II-II in FIG. 1.

As shown in FIG. 2, the internal surface of the barrel 5 is formed with a number of helical fins 7 which impart a degree of rotation to the airflow passing along the barrel 5, further increasing the turbulence of the airflow. The presence of such fins is, however, optional and is not considered to be essential to the invention.

Figure 5:
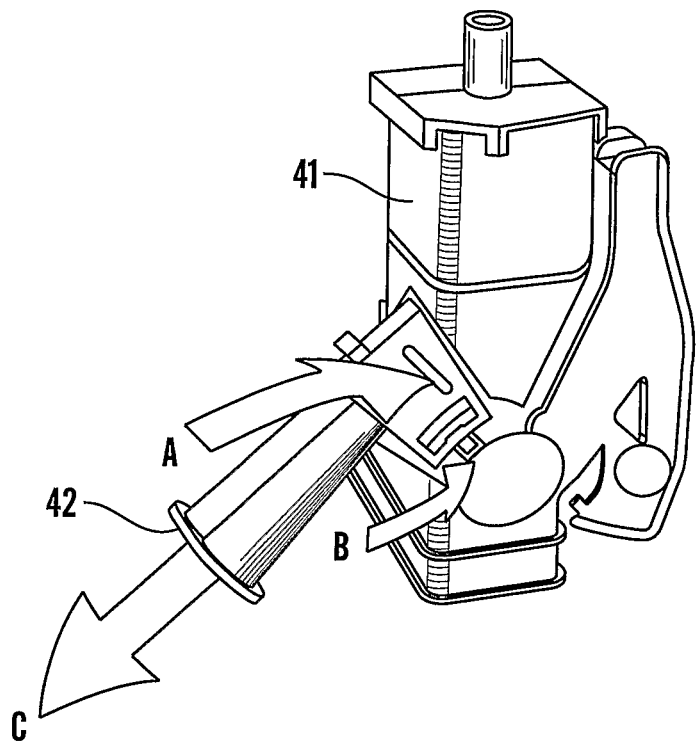
FIG. 5 is a perspective view of the internal components of a second form of dry powder inhaler according to the invention, the inhaler including a second embodiment of an airway.
Figure 6:
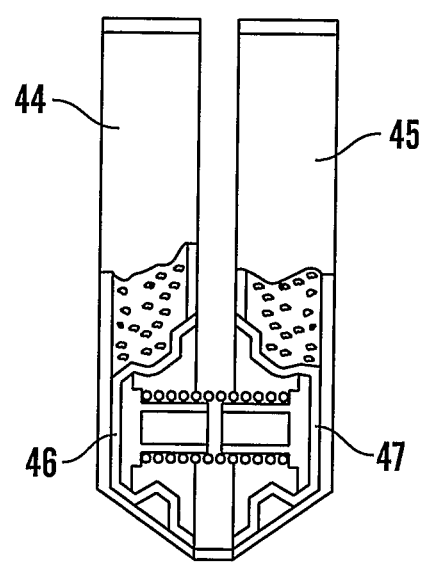
FIG. 6 is a schematic view similar to FIG. 4, but illustrating the principle of operation of the metering mechanism of the inhaler of FIG. 5.
Figure 7:
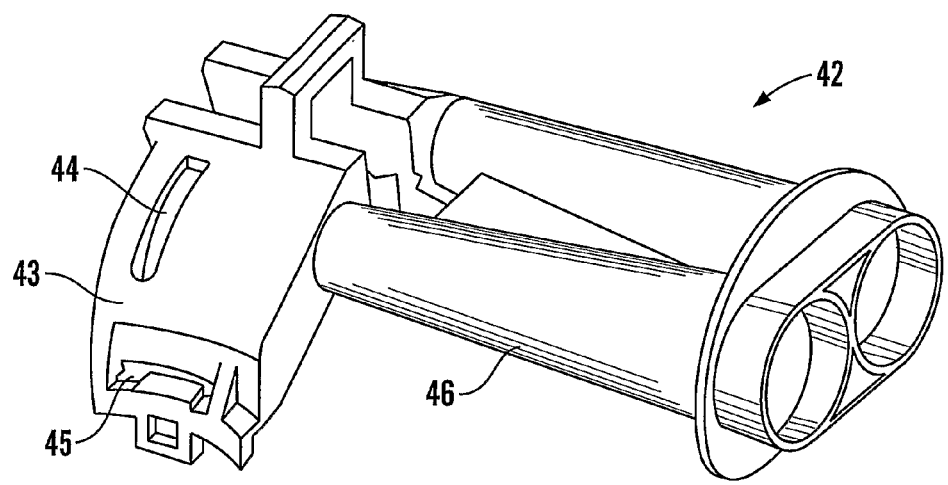
FIG. 7 is a perspective view of the second embodiment of the airway, as included in the inhaler of FIG. 5.

Referring now to FIGS. 5 to 7, a second embodiment of a dry powder inhaler and airway according to the invention is for the delivery of two different medicament formulations, which are stored in separate bulk reservoirs. In the inhaler of FIG. 5 (which shows only internal components of the inhaler), the reservoirs are housed in a central body 41 and each of the reservoirs is associated with a metering mechanism that is similar to that described above in relation to the first embodiment. A dual airway 42 (shown in FIG. 7) is fitted to the central body 41 and cooperates with the metering mechanisms to define medicament presentation regions for both of the medicaments.

The mode of operation of the metering mechanisms is illustrated in FIG. 6. It can be seen that the two reservoirs 44,45 are charged with bulk quantities of the two different powdered medicaments, and the lower ends of the reservoirs 44,45 are closed by respective frustoconical metering wheels 46,47. The wheels 46,47 are arranged in a back-to-back arrangement for rotation about a common axis. The wheels 46,47 are provided with measuring cups similar to the cups 30 of the first embodiment. The cups are charged with unit doses of medicament and undergo indexed rotation together, in a precisely analogous manner to the first embodiment, to a position at which the doses of the two medicaments are presented to the dual airway 42.

The dual airway 42 is shown most clearly in FIG. 7. As can be seen, the dual airway 42 is a single, integrally moulded component, but can be thought of as a pair of airways that are essentially similar to that of FIG. 1. The two airways are arranged side by side, one being a mirror image of the other. Each of the two airways comprises an enlarged chamber 43 at the inlet end that cooperates with the external surface of the metering mechanism to form a medicament presentation region. The chamber 43 has a primary air inlet 44 and a secondary air inlet 45. A barrel 46 of gradually increasing internal diameter extends from the chamber 43.

In use, inhalation by the user causes air to be drawn into the two chambers 43 via the respective primary and secondary air inlets 44,45 (indicated by the arrows A and B in FIG. 5 respectively). As for the first embodiment, the effect of this airflow is to flush the dose of powdered medicament from the measuring cup and to entrain the medicament in the airflow that then passes along the barrel 46 (arrow C in FIG. 5). It will be appreciated that, since the embodiment of FIGS. 5 to 7 involves two essentially separate airways, only one-half of the overall airflow is available for the entrainment, deagglomeration and aerosolisation of each medicament. It is therefore particularly important that the aerosolisation device should be effective in producing a sufficiently turbulent airflow to achieve a satisfactory fine particle fraction, even at low flow rates.

The performance of the second embodiment of the invention was investigated in the following way:

Methods

Two pharmaceutical testing methods were employed to examine the pharmaceutical performance of the airway design. A twin stage impinger (TSI)-based powder mimic test was used for rapid screening studies in the early development stages of various air inlets and airway types. According to TSI findings, initial selections were then made for further Andersen cascade impactor (ACI) testing utilising drug-containing development blends to determine the fine particle dose and fraction (FPD and FPF).

For TSI testing, blended microparticles of mannitol 15% (w/w) (containing 1% methylene blue w/w) and lactose 85% (w/w) were used. For the ACI tests, two drug powders were used, viz a steroid drug blend and a bronchodilator drug blend. The metering chambers used for these studies employed dose metering element (measuring cup) volumes of 7 mm$^3$ and 14 mm$^3$.

Results

Metered Dose Weight and Delivered Dose

Figure 8:
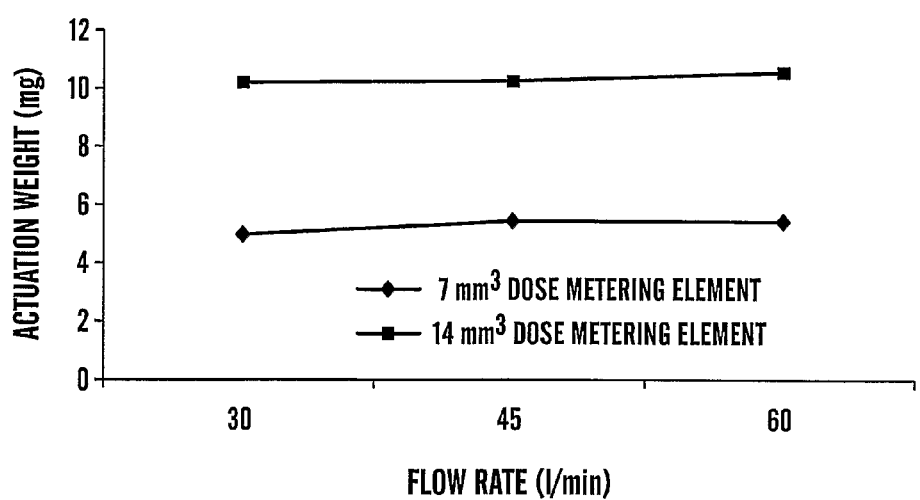
FIG. 8 shows the results of investigations of the amount of drug delivered using an airway according to the invention as a function of flow rate.

TSI drug mimic tests with two devices and five actuations (ten determinations) at each of three flow rates were carried out. FIG. 8 shows the delivered doses for both dose metering elements. The gradients for these two curves are 0.016 and 0.0143 mg/l/min, indicating only a weak dependence on flow rate over the 30 to 60 l/min range.

The ACI results for an inhaled steroid drug blend showed mean (relative standard deviation) actuation weights of 5.3 mg (5.8%) and 10.1 mg (4.8%) for the low- and high-dose product variants, respectively. The bronchodilator blend yielded a mean metered dose weight of 5.7 mg (4.8%).

Particle Size Distribution (FPD and FPF)

ACI analyses demonstrated the device deagglomeration performance, with the cut-off fine particle diameter at a flow rate of 60 l/min defined as 5 μm. The average FPF for the steroid blend was 38.5% for the 7 mm$^3$ dose metering element, and 33.5% for the 14 mm$^3$ dose metering elements. For the bronchodilator blend the average FPF was 42.3%.

In a further experiment, the airway performance was evaluated at pressure drops across the device of 2, 4 and 6 kPa. Table 1 shows the data for the most challenging blend with highest metered mass, and again shows that the airway performance is substantially independent of flow rate.

TABLE 1

ACI mean data at 2, 4 and 6 kPa pressure drop
across the inhaler device

|  | 2 kPa | 4 kPa | 6 kPa |
|---|---|---|---|
| FPD <5 μm (μg) | 74.2 | 76.2 | 81.0 |
| FPF <5 μm (%) | 40.3 | 42.2 | 43.8 |
| Flow rate (l/min) | 39.5 | 54.5 | 69.0 |

CONCLUSIONS

The airway was found to generate turbulent airflow at a low flow rate (<30 l/min). At pressure drops of 2, 4 and 6 kPa across the device and at a relatively low flow rate, the airway was able to generate efficient and flow-independent pharmaceutical performance.

The invention claimed is:

1. A dry powder inhaler comprising an airway along which, in use, air is drawn from an upstream, inlet end to a downstream, outlet end, the airway including a medicament presentation region at which, in use, a dose of medicament is presented to the airway, the medicament presentation region having a primary air inlet, and a barrel extending from the medicament presentation region to an outlet end of the airway, an inlet end of the barrel being of reduced internal dimension relative to the medicament presentation region and relative to the outlet end of the airway, such that the inlet end of the barrel constitutes a constriction of the airway;

wherein the medicament presentation region is further provided with at least one secondary air inlet from which, in use, air enters the medicament presentation region in a direction that is substantially orthogonal to a flow of air into the medicament presentation region from the primary air inlet and to a direction of flow of air along said barrel, such that the air flows from the primary and secondary air inlets meet within the medicament presentation region, at which point the air flow from the secondary air inlet has a component of motion that is orthogonal to the air flow from the primary air inlet;

wherein a ratio of the cross-sectional areas of the primary and secondary air inlets is between 5:1 and 2:1.

2. An inhaler as claimed in claim 1, wherein the medicament presentation region of the airway comprises a substantially enclosed chamber having walls, the walls of the substantially enclosed chamber defining the primary and secondary air inlets.

3. An inhaler as claimed in claim 2, wherein medicament is presented to the airway by virtue of being delivered to a recess or opening in a wall of the chamber.

4. An inhaler as claimed in claim 2, wherein the primary air inlet has the form of a slot in a wall of the chamber.

5. An inhaler as claimed in claim 2, wherein the primary air inlet has the form of a slot in a wall of the chamber and the slot is disposed transverse to a longitudinal axis of the barrel.

6. An inhaler as claimed in claim 2, wherein the primary air inlet has the form of a slot formed in a wall of the chamber that is opposite to that to which the dose of medicament is presented, such that air is drawn into the chamber with a component of its motion that is directed towards the wall of the chamber at which the medicament is presented.

7. An inhaler as claimed in claim 2, wherein the secondary air inlet has the form of a slot.

8. An inhaler as claimed in claim 2, wherein the secondary air inlet is provided in a wall of the chamber that is orthogonal to a wall at which the medicament is presented.

9. An inhaler as claimed in claim 1, wherein the inlet end of the barrel has an internal diameter of from 2 mm to 4 mm, and an outlet end of the barrel has an internal diameter of from 4 mm to 8 mm.

10. An inhaler as claimed in claim 1, wherein the barrel has internal walls that are provided with grooves or fins.

11. An inhaler as claimed in claim 1, wherein the cross-sectional area of the primary air inlet is greater than 2 $mm^2$.

12. An inhaler as claimed in claim 1, wherein the cross-sectional area of the primary air inlet is less than 10 $mm^2$.

13. An inhaler as claimed in claim 1, wherein the cross-sectional area of the secondary air inlet is greater than 0.5 $mm^2$.

14. An inhaler as claimed in claim 1, wherein the cross-sectional area of the secondary air inlet is less than 5 $mm^2$.

15. An inhaler as claimed in claim 1, wherein the primary and secondary air inlets are positioned such that, in normal use, they avoid occlusion by a user.

16. A dry powder inhaler as claimed in claim 1 wherein a diameter of the barrel increases gradually from the inlet end to an outlet end of the barrel.

17. An inhaler as claimed in claim 16, which is charged with a medicament selected from $\beta_2$-agonists, non-selective beta-stimulants, xanthine bronchodilators, anticholinergics, mast cell stabilisers, bronchial anti-inflammatory agents, and steroids.

18. An inhaler as claimed in claim 16, which comprises a plurality of separate airways along which, in use, air is drawn from an upstream, inlet end to a downstream, outlet end, each airway including a medicament presentation region at which, in use, a dose of medicament is presented to the airway, each medicament presentation region having a primary air inlet, and a barrel extending from its respective medicament presentation region to the respective outlet end of the airway, an inlet end of each barrel being of reduced internal dimension relative to the respective medicament presentation region and relative to a respective outlet end of the barrel, such that each inlet end of the barrels constitutes a constriction of the respective airway;

wherein each medicament presentation region is further provided with at least one secondary air inlet from which, in use, air enters the medicament presentation regions in a direction that is substantially orthogonal to a flow of air into the medicament presentation regions from the primary air inlets and to a direction of flow of air along said barrels.

19. An inhaler as claimed in claim 18, which is charged with a combination of medicaments selected from the group consisting of beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol.

20. An inhaler as claimed in claim 1, which is charged with a medicament selected from $\beta_2$-agonists, non-selective beta-stimulants, xanthine bronchodilators, anticholinergics, mast cell stabilisers, bronchial anti-inflammatory agents, and steroids.

21. An inhaler as claimed in claim 1, which comprises a plurality of separate airways along which, in use, air is drawn from an upstream, inlet end to a downstream, outlet end, each airway including a medicament presentation region at which, in use, a dose of medicament is presented to the airway, each medicament presentation region having a primary air inlet, and a barrel extending from its respective medicament presentation region to the respective outlet end of the airway, an inlet end of each barrel being of reduced internal dimension relative to the respective medicament presentation region and relative to a respective outlet end of the barrel, such that each inlet end of the barrels constitutes a constriction of the respective airway;

wherein each medicament presentation region is further provided with at least one secondary air inlet from which, in use, air enters the medicament presentation regions in a direction that is substantially orthogonal to a flow of air into the medicament presentation regions from the primary air inlets and to a direction of flow of air along said barrels.

22. An inhaler as claimed in claim 21, which is charged with a combination of medicaments selected from the group consisting of beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol.

23. An inhaler as claimed in claim 1 wherein the primary air inlet is positioned on the airway for exposure to ambient air and allows air to flow external of the inhaler into the medicament presentation region during use.

24. A dry powder inhaler comprising an airway along which, in use, air is drawn from an upstream, inlet end to a downstream, outlet end, the airway including a medicament presentation region at which, in use, a dose of medicament is presented to the airway, the medicament presentation region having a primary air inlet, and a barrel extending from the medicament presentation region to an outlet end of the airway, an inlet end of the barrel being of reduced internal dimension relative to the medicament presentation region and relative to the outlet end of the airway, such that the inlet end of the barrel constitutes a constriction of the airway;

wherein the medicament presentation region is further provided with at least one secondary air inlet, and a ratio of the cross-sectional areas of the primary and secondary air inlets is between 5:1 and 2:1.

25. An inhaler as claimed in claim 24, wherein the cross-sectional area of the primary air inlet is greater than 2 mm$^2$.

26. An inhaler as claimed in claim 24, wherein the cross-sectional area of the primary air inlet is less than 10 mm$^2$.

27. An inhaler as claimed in claim 24, wherein the cross-sectional area of the secondary air inlet is greater than 0.5 mm$^2$.

28. An inhaler as claimed in claim 24, wherein the cross-sectional area of the secondary air inlet is less than 5 mm$^2$.

29. An inhaler as claimed in claim 24, wherein the primary and secondary air inlets are positioned such that, in normal use, they avoid occlusion by a user.

30. An inhaler as claimed in claim 24, which is charged with a medicament selected from $\beta_2$-agonists, non-selective beta-stimulants, xanthine bronchodilators, anticholinergics, mast cell stabilisers, bronchial anti-inflammatory agents, and steroids.

31. An inhaler as claimed in claim 24, which comprises a plurality of separate airways along which, in use, air is drawn from an upstream, inlet end to a downstream, outlet end, each airway including a medicament presentation region at which, in use, a dose of medicament is presented to the airway, each medicament presentation region having a primary air inlet, and a barrel extending from its respective medicament presentation region to the respective outlet end of the airway, an inlet end of each barrel being of reduced internal dimension relative to the respective medicament presentation region and relative to a respective outlet end of the barrel, such that each inlet end of the barrels constitutes a constriction of the respective airway;

wherein each medicament presentation region is further provided with at least one secondary air inlet from which, in use, air enters the medicament presentation regions in a direction that is substantially orthogonal to a flow of air into the medicament presentation regions from the primary air inlets and to a direction of flow of air along said barrels.

32. An inhaler as claimed in claim 31, which is charged with a combination of medicaments selected from the group consisting of beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol.

* * * * *